(12) United States Patent
Sherry et al.

(10) Patent No.: US 12,121,025 B2
(45) Date of Patent: Oct. 22, 2024

(54) ANTIMICROBIAL COMPOSITION

(71) Applicant: The Procter & Gamble Company, Cincinnati, OH (US)

(72) Inventors: Alan Edward Sherry, Newport, KY (US); Anthony Wayne Ball, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 8 days.

(21) Appl. No.: 17/830,374

(22) Filed: Jun. 2, 2022

(65) Prior Publication Data

US 2022/0386600 A1 Dec. 8, 2022

(30) Foreign Application Priority Data

Jun. 4, 2021 (EP) ...................................... 21177689
Apr. 5, 2022 (EP) ...................................... 22166642

(51) Int. Cl.
*A01N 37/02* (2006.01)
*A01N 31/02* (2006.01)
*A01N 31/14* (2006.01)
*A01P 1/00* (2006.01)

(52) U.S. Cl.
CPC ............. *A01N 37/02* (2013.01); *A01N 31/02* (2013.01); *A01N 31/14* (2013.01); *A01P 1/00* (2021.08)

(58) Field of Classification Search
CPC ........... A01P 1/00; A01N 25/30; A01N 25/34; A01N 31/02; A01N 31/14; A01N 37/02; A01N 37/36; A01N 39/00; A61L 2/18; A61L 2101/40
See application file for complete search history.

(56) References Cited

U.S. PATENT DOCUMENTS

| 2015/0272969 A1 | 10/2015 | Ahmed et al. |
| 2017/0173196 A1* | 6/2017 | Sherry .................... A61L 2/186 |
| 2018/0371376 A1 | 12/2018 | Hayward |
| 2019/0270951 A1 | 9/2019 | Hardy et al. |
| 2020/0352836 A1 | 11/2020 | Agarkhed et al. |

FOREIGN PATENT DOCUMENTS

| CN | 108651710 A | 10/2018 |
| WO | 2019143882 A1 | 7/2019 |
| WO | 2020210789 A1 | 10/2020 |
| WO | 2001094513 A1 | 12/2021 |

OTHER PUBLICATIONS

PCT Search Report and Written Opinion for PCT/US2022/031712 dated Aug. 31, 2022, 13 pages.
Extended European Search Report and Search Opinion; Application No. 22166642.3 ; dated Aug. 25, 2022; 7 pages.

* cited by examiner

*Primary Examiner* — Umamaheswari Ramachandran
(74) *Attorney, Agent, or Firm* — George H. Leal; Carolyn S. Powell

(57) ABSTRACT

Antimicrobial compositions and methods of use thereof are described. The antimicrobial compositions have an acid system, an anionic surfactant system and 2-phenoxyethanol and/or a fragrance. The acid system includes at least 30 wt % of octanoic acid and a secondary acid. The anionic surfactant system includes at least 60 wt % of octyl sulfate and a secondary surfactant having a moiety with a carbon chain length with at least ten carbon atoms. The antimicrobial composition has a pH of from about 1.5 to about 5 as measured at 20° C.

18 Claims, No Drawings

ANTIMICROBIAL COMPOSITION

FIELD OF THE INVENTION

The present invention is in the field of antimicrobial compositions. In particular, it relates to a composition containing a surfactant system, an acid system comprising octanoic acid, and methods of using the composition to provide fast disinfection on hard surfaces.

BACKGROUND OF THE INVENTION

There is an ever-increasing demand for antimicrobial products. The prior art describes a great variety of antimicrobial products, see for example WO2020/210789 A1 and WO2001/094513 A1. Still there is a need for easy-to-use, fast-acting antimicrobial products with a broad-spectrum of biocidal activity. Some of the antimicrobial products have a malodour associated to them. One of the objectives of the present invention is to provide a fast-acting broad-spectrum antimicrobial product which has pleasant smell associated to it.

Sometimes it is desirable to have the compositions in concentrated form to reduce packaging and transport costs and to reduce environmental impact. The formulation of antimicrobial concentrated compositions is not straight forward, not only the concentrate should be stable on storage but it should also be stable and not lose its biocidal properties when diluted in water of different hardness. Thus, another objective of the present invention is to provide a composition with biocidal properties that is stable as a concentrate (physical & chemical stability) and does not become unstable when diluted. Another objective is to provide an antimicrobial composition that is effective when sprayed from a variety of spraying devices, including sprayers that deliver small droplet sizes.

SUMMARY OF THE INVENTION

According to the first aspect of the invention, there is provided an antimicrobial composition. The composition comprises an anionic surfactant system, an acid system and 2-phenoxyethanol and/or a fragrance. The composition has a pH of from about 1.5 to about 5 or from about 2 to about 4 as measured at 20° C.

The composition of the invention comprises:
a) an acid system, the acid system comprises at least 30% by weight of the acid system of octanoic acid. It also comprises a secondary acid preferably selected from $C_1$-$C_{10}$ mono-, di- and triprotic organic acids and inorganic acids, and polymeric acids;
b) an anionic surfactant system, the anionic surfactant system comprises at least 60% by weight of the surfactant system of octyl sulfate and a secondary surfactant having a moiety comprising a carbon chain with at least ten carbon atoms preferably at least 5% by weight of the surfactant system comprises dodecyl sulfate; and
c) a fragrance and/or 2-phenoxyethanol;
wherein the composition has a pH from about 1.5 to about 5 as measured at 20° C.

The composition is suitable to be in the form of a concentrate to be diluted before use or in ready-to-use form.

According to the second and third aspects of the invention, there are provided methods to clean an inanimate surface, preferably a hard surface with the composition of the invention. Lastly, there is provided the use of the composition to provide fast disinfection.

The elements of the invention described in relation to the first aspect of the invention apply mutatis mutandis to the other aspects of the invention.

DETAILED DESCRIPTION OF THE INVENTION

The present invention envisages an antimicrobial composition that can be used in the form of a concentrate to be diluted before use or in ready-to-use form. The composition presents fast biocidal action over a broad spectrum of microorganisms. The concentrate is stable in store and upon dilution.

As used herein, the articles including "the," "a" and "an" when used in a claim or in the specification, are understood to mean one or more of what is claimed or described.

As used herein, the terms "include," "includes" and "including" are meant to be non-limiting.

The terms "microorganism" or "microbe" as used herein are intended to include cellular organisms, both unicellular and multicellular that are less than 5 mm in length; this includes but is not limited to bacteria including spore forming bacteria, fungi, prions, enveloped and non-enveloped viruses, archaea, protists, protozoa or oocysts formed by protozoa, green algae, plankton, planarian, amoebas and yeasts, or spores formed by any of these. The terms "microorganism" or "microbe" include the single or planktonic microbes that may contaminate surfaces, as well as communities of microbes that grow as biofilms on surfaces.

The term "antimicrobial" as used herein refers to a compound that exhibits microbicide or microbiostatic properties that enables the compound to kill, destroy, inactivate, or neutralize a microorganism; or to mitigate, prevent, or reduce the growth, ability to survive, or propagation of a microorganism. In the context of antimicrobial, the term "treat" means to kill, destroy, inactivate, or neutralize a microorganism; or to prevent or reduce the growth, ability to survive, or propagation of a microorganism The term "substantially free of" or "substantially free from" as used herein refers to either the complete absence of an ingredient or a minimal amount thereof merely as impurity or unintended byproduct of another ingredient. A composition that is "substantially free" of/from a component means that the composition comprises less than about 0.01%, or less than about 0.001%, or even 0%, by weight of the composition, of the component.

In this description, all concentrations and ratios are on a weight basis of the composition unless otherwise specified.

Unless otherwise noted, all component or composition levels are in reference to the active portion of that component or composition, and are exclusive of impurities, for example, residual solvents or by-products, which may be present in commercially available sources of such components or compositions.

All measurements are performed at 20° C. unless otherwise specified.

Composition

The composition of the present invention may be formulated as a concentrate or ready-to-use composition. The composition of the present invention may deliver cleaning and shine benefits on inanimate surfaces, both hard and soft surfaces. The composition of the present invention is an antimicrobial composition and delivers improved antimicrobial activity on hard and soft surfaces. The composition of the present invention may deliver cleaning benefits and shine benefits as well as antimicrobial benefits on hard and soft surfaces. Preferably, the composition of the present disclosure is a liquid composition, more preferably an aqueous liquid composition. As a concentrate execution, the composition comprises less than 80% by weight of the composition of water or from 40% to 60% by weight of the composition of water. As a ready-to-use execution, the composition comprises more than 80% by weight of the composition of water or from 90% to 99% by weight of the composition of water.

Concentrates may be diluted with water in order to provide an in-use solution having a desired level of detersive properties or other properties, including antimicrobial properties. The desired antimicrobial properties may depend on the challenge posed by the target microorganism; for example, enveloped viruses are more susceptible to inactivation than non-enveloped viruses, and spore-forming organisms are very resistant to chemical inactivation. Each organism type presents a different challenge and may call for a different level of dilution (or none) in order to achieve the desired antimicrobial activity.

The water used to dilute the concentrate (water of dilution) can be available at the locale or site of dilution. The water of dilution may contain varying levels of hardness depending upon the locale. Service waters available from various municipalities have varying levels of hardness. It is desirable to provide a concentrate that can handle the hardness levels found in the service water of various municipalities. The water of dilution may have a hardness ranging from about zero to at least about 400 ppm hardness (as $CaCO_3$).

Concentrated solutions may provide for improved economics to the manufacturer and to the user as they may comprise less water and may use less packaging material on a per-use basis, as compared to ready-to-use compositions. A concentrated composition may be diluted with water at a weight ratio of composition to water ranging from about 1:1.5 to about 1:250, or from about 1:4 to about 1:100. The terms "in-use composition" or "in-use diluted composition" refer to concentrated compositions that have been diluted with water prior to use.

Alternatively, the compositions may be in a ready-to-use form, preferably to be delivery in spray form. Ready-to-use compositions provide additional degrees of freedom to further enhance cidal activity via solvents, especially glycol ethers including ethylene glycol n-hexyl ether and 2-phenoxyethanol. Enhanced cidal activity can be manifested via a reduction in contact time needed to achieve complete kill/inactivation versus specific microorganisms or via a broadening of scope of microorganisms that can be killed/inactivated, or via reduction of the amount of actives or via all of them.

The compositions disclosed herein provide short-contact-time antimicrobial benefits, e.g., from about 5 seconds to about 5 minutes or from about 10 seconds to about 3 minutes, or from 15 seconds to about 2 minutes or from 15 to 30 seconds.

The composition may comprise other antimicrobial agents or be free of other antimicrobial agents. Other antimicrobial agents include ionic silver salts (e.g., silver dihydrogen citrate and silver nitrate), hydrogen peroxide, C12-16 benzalkonium salts (e.g., chloride, bromide and saccharinate salts), dialkyldimethylammonium salts (e.g., C8-C8, C8-C10 & C10-C10 chain lengths, chloride, bromide, bicarbonate and carbonate salts), benzethonium chloride (or bromide), cetyl trimethyl ammonium chloride (or bromide), and mixtures thereof. Other antimicrobial agents include glutaraldehyde, zinc 2-pyridinethiol-1-oxide, copper sulfate pentahydrate, iodine, iodine salts, butoxypolypropoxypolyethoxyethanol iodine complex, polyvinylpyrrolidone-iodine complex, polyvinylpyrrolidone-hydrogen peroxide complex and mixtures thereof. Hydrogen peroxide and ionic silver salts are the most preferred added antimicrobial agents for use herein. However, the composition of the invention provides fast, broad spectrum antimicrobial activity even in the absence of additional antimicrobial agents. Thus compositions free of other antimicrobial agents are preferred for use herein.

Acid System

The composition of the invention comprises an acid system. The acid system adjusts the pH of the composition to the following range: from about 1.5 to about 5, from about 2 to about 4, or from about 2.1 to about 3.5, as measured at 20° C. The acid system comprises octanoic acid as a primary acid and also comprises a secondary acid. Without being bound by theory is believed that octanoic acid provides for the fast kinetics, broad spectrum biocidal activity. The main role of the secondary acid is to reduce the pH of the composition below the pKa of octanoic acid (pKa=4.9). The lower pH ensures that octanoic acid remains almost fully protonated as deprotonation results in reduced cidal activity. The secondary acid system may provide buffering capacity and sequester transition metals, including iron, copper, manganese and the like. The secondary acid may comprise acids that are a US EPA/Health Canada registered active or a European notified antimicrobial substance.

The secondary acid comprises an organic acid, an inorganic acid, or a mixture thereof. The acid system may be substantially free of trace transition metal impurities. Preferably, the secondary acid has at least one moiety with a pKa of 4 or below at 20° C. Suitable inorganic acids include phosphoric acid, sulfuric acid, urea-sulfuric acid, hydrochloric acid, sulfamic acid, methyl sulfuric acid, hypochlorous acid, and the like. Suitable organic acids include polymeric acids comprising at least 3 carboxylic acid groups, $C_1$-$C_{10}$-organic acids comprising at least one carboxylic acid group, and organic acids that do not comprise carboxylic acid functional groups (such as imidazole derivatives or phenolic or polyphenolic compounds). Non-limiting examples of polymeric acids include polymers of acrylic acid, methacrylic acid, maleic acid, itaconic acid, and copolymers comprising acrylic acid, methacrylic acid, maleic acid, itaconic acid, and mixtures thereof. Polymeric acids may be homopolymers or copolymers having a molecular weight of about 500 g/mol or greater. The polymeric acid may have a molecular weight ranging from about 500 g/mol to about 1,000,000 g/mol, or from about 500 g/mol to about 100,000 g/mol, or from about 1,000 g/mol to about 20,000 g/mol. In one embodiment, the polymeric acids have an average molecular weight from about 800 g/mole to about 5,000 g/mol. Copolymers may be random copolymers or block copolymers. In addition to monomer units comprising carboxylic acid groups, the copolymers may also include one or more other monomers, such as styrene, styrene sulfonate, acrylic ester, acrylamide, olefin sulfonate, and olefin acetate.

Non-limiting examples of $C_1$-$C_{10}$ organic acids include formic acid, acetic acid, benzoic acid, malonic acid, citric acid, maleic acid, fumaric acid, succinic acid, lactic acid, malic acid, tartaric acid, gluconic acid, glutaric acid, adipic acid, butane tetracarboxylic acid, and the like. The organic acid may be derived from a renewable, plant-based feedstock and may be produced using natural processes, such as fermentation; examples include bio-based acetic acid, bio-based citric acid, bio-based lactic acid and bio-based succinic acid, and the like. The organic acid may have food-use pedigree or be Generally Regarded As Safe (GRAS) or as a food additive by the US Food & Drug Administration (FDA). The organic acid is preferably approved as a food use inert by the US EPA and by European regulatory agencies.

The acid system comprises at least 30% by weight thereof of octanoic acid. In the case of the concentrate, the composition comprises from about 10% to about 30%, from about 12% to about 22% by weight of the composition of the acid system. The acid system comprises from about 30% to about 50%, from about 30% to about 45% by weight thereof of octanoic acid. The secondary acid can have a pKa of 4 or below at 20° C., and for food-use disinfection applications can be selected from citric acid, lactic acid and mixtures thereof.

In the case of the ready-to-use composition, the composition comprises from about 0.3% to about 6% or from about 0.5% to about 4% by weight of the composition of the acid system. The acid system comprises from about 30% to about 45% or from about 30% to about 35% by weight thereof of octanoic acid. The secondary acid can have a pKa of 4 or below at 20° C., preferably, the secondary acid is selected from citric acid, lactic acid and mixtures thereof.

Anionic Surfactant System

The compositions of the present disclosure comprise an anionic surfactant system. By "anionic surfactant system" is herein meant a system comprising at least two different anionic surfactants. The surfactant system comprises octyl sulfate, preferably in the form of sodium octyl sulfate, as a main surfactant and a secondary anionic surfactant having a hydrophobic moiety comprising a carbon chain length with at least ten carbon atoms, with at least eleven carbon atoms or with twelve carbon atoms. Preferably the surfactant system comprises sodium dodecyl sulfate (e.g., Na C12 AS) or sodium lauryl sulfate (e.g., Na C12-14 AS) as a secondary surfactant. Specific ratios of octyl sulfate to dodecyl sulfate/lauryl sulfate are used to provide phase and chemical stability, in both concentrated and diluted form. Additionally, the combination of octyl sulfate and dodecyl sulfate at ratios disclosed herein also helps drive cidal activity of the concentrates upon dilution.

Without wishing to be bound by theory, it is believed that octyl sulfate provides fast biocidal kinetics and also acts as a hydrotrope driving enhanced dissolution of octanoic acid in the concentrate. The role of the secondary anionic surfactant is to provide solubility to the concentrate upon dilution in water. It has been found that sodium octyl sulfate readily solubilizes octanoic acid (solubility in water=0.07 g/100 ml at 25° C. in absence of sodium octyl sulfate) in the concentrated form. However, sodium octyl sulfate is less effective in solubilizing octanoic acid following a significant dilution in water. The higher the water content, the more difficult it is to solubilize octanoic acid with octyl sulfate. Longer chain length surfactants are effective to improve solubility at high water dilutions. Sodium dodecyl sulfate and sodium lauryl sulfate are particularly effective in this respect. Other optional long-chain (C12 chain length or greater) secondary surfactants can also be used; examples include but are not limited to, sodium C14-17 paraffin sulfonate (14 to 17 carbon atoms in the hydrophobic moiety), sodium dodecyl benzene sulfonate (18 carbon atoms in the hydrophobic moiety), sodium dodecyl diphenyl ether disulfonate (24 carbon atoms in the hydrophobic moiety), sodium lauryl ether sulfate (12-14 carbon atoms in the hydrophobic moiety), and the like. So as to comply with regulations associated with cleaning and disinfecting products on food contact surfaces, the second surfactant is preferably an approved food use inert (https://iaspub.epa-.gov/apex/pesticides/f?p=INERTFINDER:1:0::NO:1).

Sodium dodecyl sulfate/sodium lauryl sulfate is preferred for use herein.

The anionic surfactant system comprises at least 60% by weight of the system of octyl sulfate. More specifically, concentrate and ready-to-use compositions herein comprise from about 60% to about 90% or from about 75% to about 90% by weight of the anionic surfactant system of octyl sulfate salt. Preferably, the anionic system also comprises at least 5% by weight of the anionic system of sodium dodecyl sulfate or sodium lauryl sulfate (lauryl sulfate generally comprises ~65-75% C12 chain length+~25-35% C14 chain length with minor or negligible levels of C10 and C16 chain length). Concentrate compositions herein may comprise from about 5% to about 40% or from about 10% to about 25% by weight of the anionic surfactant system of either dodecyl sulfate salt or lauryl sulfate salt. The weight ratio of octyl sulfate to dodecyl sulfate can be from about 4:1 to about 10:1. Ready-to-use compositions herein may comprise from about 5% to about 40% or from about 10% to about 25% by weight of the anionic surfactant system of either dodecyl sulfate salt or lauryl sulfate salt. The ratio of octyl sulfate to dodecyl sulfate can be from about 2:1 to about 10:1.

Fragrance

The composition comprises a fragrance. The fragrance is a mixture of odorant raw materials, such as aromatic natural oils and aromatic chemicals, which taken together form a complex scent that delivers a number of benefits. These benefits may include the coverage of product base odor, scenting the product itself, and lingering scent radiating from the surface into the air after cleaning. When the composition is sprayed, the benefit may also include the delivery of scent to the air when spraying the composition on a surface, and the delivery of scent to the air while wiping the composition on the surface. The fragrance may comprise at least 3, at least 5, at least 7, at least 11, or at least 15 fragrance raw materials.

The fragrance may comprise at most 50%, or at most 40%, or at most 30%, for example from 0% to 20%, or from 0.01% to 10%, or from 0.02% to 5%, per weight of raw materials comprising an α, β-unsaturated aldehyde function, an α, β-unsaturated ketone function, and/or an ester function.

For the purpose of the invention, an aromatic aldehyde/ketone wherein the aromatic ring is adjacent to the aldehyde or ketone group (e.g. anisic aldehyde or methyl β-naphthyl ketone) is considered as an α, β-unsaturated aldehyde/ketone.

The fragrance raw materials of the fragrance of the composition of the invention may comprise at most 50%, or at most 40%, or at most 30% for example from 0% to 20%, or from 0.01% to 10%, or from 0.02% to 5% per weight of fragrance raw materials selected from benzyl acetate, methyl salicylate, allyl amyl glycolate, benzyl propionate, pomarose, methyl dihydrojasmonate, heliotropin, anisic aldehyde, delta damascone, amyl butyrate, iso-amyl iso-butyrate, b-ionone, carvone, iso-butyl iso butanoate, methyl b-naphtyl ketone, citronellyl butyrate, iso-propyl miristate.

The fragrance of the composition of the invention may comprise at least 20% per weight, in particular at least 30%, or at least 40%, or at least 50%, or at least 60%, or at least 70% for example from 80% to 100%, or from 90% to 99.9% per weight of raw materials comprising an α, β-saturated aldehyde function, an α, β-saturated ketone function, an alcohol function, an ether function, a nitrile function, and/or being a terpene.

For the purpose of the invention an α, β-saturated aldehyde function is an aldehyde function without unsaturation in the α or β position.

For the purpose of the invention an α, β-saturated ketone function is a ketone function without unsaturation in the α or β position.

The fragrance of the composition of the invention may comprise at least 20% per weight, in particular at least 30%, or at least 40%, or at least 50%, or at least 60%, or at least 70% for example from 80% to 100%, or from 90% to 99.9% per weight of raw materials which do not comprise α, β-unsaturated aldehyde function, an α, β-unsaturated ketone function, and/or an ester function.

The fragrance of the composition of the invention may comprise at least 20% per weight, in particular at least 30%, or at least 40%, or at least 50%, or at least 60%, or at least 70% for example from 80% to 100%, or from 90% to 99.9% per weight of raw materials which comprise α, β-saturated aldehyde function, an α, β-saturated ketone function, an alcohol function, an ether function, a nitrile function, and/or are a terpene and which do not comprise an α, β-unsaturated aldehyde function, an α, β-unsaturated ketone function, and/or an ester function.

The fragrance of the composition of the invention may comprise at least 20% per weight, in particular at least 30%, or at least 40%, or at least 50%, or at least 60%, or at least 70% for example from 80% to 100%, or from 90% to 99.9% per weight of raw materials selected from d-muscenone 1, ambrox, polysantol, phenylethyl dimethyl carbinol, hydroxycitronellal, undecavertol, citronellol, linalool, p-cresyl methyl ether, cis-3-hexenol, clonal, limonene, tobacarol 2, tobacarol 3, tobacarol 1, b-naphthyl methyl ether. Other fragrances suitable for use in the composition of the invention are described in EP 1 493 803 A1 and WO 2002/06437 A1.

The composition may comprise from 0.1% to 5%, or from 0.2% to 4%, or even from 0.3% to 4% of fragrance by weight of the composition.

Especially preferred fragrance raw materials to be used in the compositions of the inventions are those listed in Tables 1 and 2.

TABLE 1

| CAS Number | Chemical Name | OtherName |
|---|---|---|
| Exemplary Fragrance Raw Materials | | |
| Aliphatic, linear alpha, beta-unstaurated aldehydes, acids, and related alcohols | | |
| 3913-71-1 | 2-Decenal | 2-Decenal |
| 6728-26-3 | Hexen-2-al | 2-Hexenal, (2E)- |
| 111-79-5 | Methyl 2-nonenoate | 2-Nonenoic acid, methyl ester |
| 111-80-8 | Methyl 2-nonynoate | 2-Nonenoic acid, methyl ester |
| 111-12-6 | Methyl 2-octynoate | |
| Aliphatic acyclic acetals | | |
| 28069-74-1 | Acetaldehyde ethyl cis-3-hexenyl acetal | 3-Hexene, 1-(1-ethoxyethoxy)-, (3Z)- |
| 7492-66-2 | 1, 1-diethoxy-3, 7-dimethylocta-2,6-diene | 2,6-Octadiene, 1,1-diethoxy-3,7-dimethyl- |
| 10022-28-3 | Octanal dimethyl acetal | Octane, 1,1-dimethoxy- |
| Aliphatic acyclic and alicyclic terpenoid tertiary alcohols and structurally related substances | | |
| 151-05-3 | Alpha,alpha-Dimethylphenethyl acetate | Benzeneethanol,alpha.,.alpha,-dimethyl-, acetate |
| 10094-34-5 | Alpha,alpha-Dimethylphenethylbutyrate | Butanoic acid, 1,1-dimethyl-2-phenylethy ester |
| 78-70-6 | Linalool | 1,6-Octadien-3-ol, 3,7-dimethyl- |
| 115-95-7 | Linalyl acetate | 1,6-Octadien-3-ol, 3,7-dimethyl-, acetate |
| 7212-44-4 | Nerolidol (isomer unspecified) | 1,6,10-Dodecatrien-3-ol, 3,7,11-trimethyl- |
| 98-55-5 | Alpha-Terpineol | 3-Cyclohexene-a-methanol, .alpha.,.alpha.,4 trimethyl- |
| 8007-35-0 | Terpinyl acetate (Isomer mixture) | Terpineol, acetate |
| 78-69-3 | Tetrahydrolinalool | 3-Octanol, 3,7-dimethyl- |
| Aliphatic acyclic diols, triols, and related agents | | |
| 102-76-1 | (tri-)Acetin | 1,2,3-Propanetriol, triacetate |
| Aliphatic and alicyclic hydrocarbons | | |
| 87-44-5 | Beta-Caryophyllene | Bicyclo[7.2.0]undec-4-ene,4,1 1,1 1-trimethyl-8-methylene-, (1R,4E,9S)- |
| 98-85-4 | p-Mentha-1,4-diene | 1,4-Cyclohexadiene, 1-methyl-4-(1-methylethyl)- |

TABLE 1-continued

Exemplary Fragrance Raw Materials

| CAS Number | I Chemical Name | I OtherName |
|---|---|---|
| 80-56-8 | Alpha-Pinene | Bicyclo[3.1.1]hept-2-ene,2,6,6-trimethyl- |
| 127-91-3 | Beta-Pinene | Bicyclo[3.1.1]hept-2-ene, 2,6,6-trimethyl- |
| 586-62-9 | Terpinolene | Cyclohexene, 1-methyl-4-(1-methylethylidene)- |

Aliphatic and aromatic ethers

| | | |
|---|---|---|
| 101-84-8 | Diphenyl ether | Benzene, 1,1'-oxybis- |
| 470-82-6 | Eucalyptol | 2-Oxabicyclo[2.2.2]octane, 1,3,3-trimethyl- |
| 104-98-8 | p-Methylanisole | Benzene, 1-methoxy-4-methyl- |
| 16409-43-1 | Tetrahydro-4-methyl-2-(2-methylpropen-1-yl)pyran | 2H-Pyran, tetrahydro-4-methyl-2-(2-methyl 1-propenyl)- |

Aliphatic branched-chain unsaturated alcohols, aldehydes, acids, and related esters

| | | |
|---|---|---|
| 106-23-0 | Citronellal | 6-Octenal, 3,7-dimethyl- |
| 106-25-2 | Nerol | 2,6-Octadien-1-ol, 3,7-dimethyl-, (2Z)- |

Aliphatic di-and trienals and related alcohols, acids, and esters

| | | |
|---|---|---|
| 3025-30-7 | Ethyl (2E,4Z)-2,4-decadienoate | 2,4-Decadienoic acid, ethyl ester, (2E,4Z)- |
| 557-48-2 | Nona-2-trans-6-cis-dienal | 2,6-Nonadienal, (2E,6Z)- |

Aliphatic lactones

| | | |
|---|---|---|
| 706-14-9 | gamrna-Decalactone | 2(3H)-Furanone, 5-hexyldihydro- |
| 105-21-5 | gamrna-Heptalactone | 2(3H)-Furanone, dihydro-5-propyl- |
| 695-06-7 | gamma-Hexalactone | (3H)-Furanone, 5-ethyldihydro- |
| 3301-94-8 | Hydroxynonanoic acid, delta lactone | |
| 710-04-3 | 5-Hydroxyundecanoic acid lactone | 2H-Pyran-2-one, 6-hexyltetrahydro- |
| 28645-51-4 | Oxacycloheptadec-10-ene-2-one | Oxacycloheptadec-10-en-2-one |
| 104-61-0 | gamrna-Nonalactone | 2(3H)-Furanone, dihydro-5-pentyl- |
| 104-50-7 | gamrna-Octalactone | 2(3H)-Furanone, 5-butyldihydro- |
| 106-02-5 | omega-Pentadecalactone | Oxacyclohexadecan-2-one |
| 104-67-6 | gamma-Undecalactone | 2(3H)-Furanone, 5-heptyldihydro- |

Aliphatic secondary alcohols, ketones and related esters and acetals

| | | |
|---|---|---|
| 81925-81-7 | 5-Methyl-2-hepten-4-one | |
| 110-93-0 | 6-Methyl-5-hepten-2-one | 5-Hepten-2-one, 6-methyl- |

Allyl esters

| | | |
|---|---|---|
| 123-68-2 | Ally hexanoate | Hexanoic acid, 2-propenyl ester |

Alphatic primary alcohols, aldehydes, carboxylic acids, acetals and esters

| | | |
|---|---|---|
| 105-53-3 | Diethyl malonate | Propanedioic acid, diethyl ester |
| 141-97-9 | Ethyl acetoacetate | Butanoic acid, 3-oxo-, ethyl ester |
| 105-95-3 | Ethylene brassylate | 1,4-Dioxacy cloheptadecane-5,17-dione |
| 107-75-5 | Hydroxycitronellal | Octanal, 7-hydroxy-3,7-dimethyl- |
| 107-74-4 | Hydroxycitronellol | 1,7-Octanediol, 3,7-dimethyl- |
| 705-86-2 | delta-Decalactone | 2H-Pvran-2-one, tetrahydro-6-pentvl- |
| 77-93-0 | Triethylcitrate | 1,2,3-Propanetricarboxylic acid, 2-hydroxy-triethyl ester |

Anthranilate derivatives

| | | |
|---|---|---|
| 134-20-3 | Methyl anthranilate | Benzoic acid, 2-amino-, methyl ester |
| 85-91-6 | Methyl N-methylanthranilate | Benzoic acid, 2-(methylamino)-, methyl ester |

Aromatic hydrocarbons

| | | |
|---|---|---|
| 99-87-6 | p-Cymene | Benzene, 1-methyl-4-(1-methylethyl)- |

Aromatic substituted secondary alcohols, ketones, and related ester

| | | |
|---|---|---|
| 98-86-2 | Acetophenone | Ethanone, 1-phenyl- |
| 122-00-9 | 4'-Methylacetophenone | Ethanone, 1(4-methylphenyl)- |
| 93-92-5 | alpha-Methylbenzyl acetate | Benzenemethanol, alpha.-methyl-, acetate |
| 98-85-1 | alpha-Methylbenzyl alcohol | Benzenemethanol, alpha.-methyl- |
| 93-08-3 | Methyl beta-naphthyl ketone | Ethanone, 1-(2-naphthalenyl)- |

Benzyl derivatives

| | | |
|---|---|---|
| 100-52-7 | Benzaldehyde | Benzaldehyde |
| 140-11-4 | Benzyl acetate | Acetic acid, phenylmethyl ester |
| 100-51-6 | Benzyl alcohol | Benzenemethanol |
| 103-37-7 | Benzyl butyrate | Butanoic acid, phenylmethyl ester |
| 103-28-6 | Benzyl isobutyrate | Propanoic acid, 2-methyl-, phenylmethyl ester |
| 122-63-4 | Benzvl propionate | Propanoic acid, phenylmethyl ester |

TABLE 1-continued

Exemplary Fragrance Raw Materials

| CAS Number | Chemical Name | OtherName |
|---|---|---|
| 122-03-2 | Cuminaldehyde | Benzaldehyde, 4-(1-methylethyl)- |
| 93-89-0 | Ethyl benzoate | Benzoic acid, ethyl ester |
| 93-58-3 | Methyl benzoate | Benzoic acid, methyl ester |

Carvone and structurally related substances

| CAS Number | Chemical Name | OtherName |
|---|---|---|
| 20777-49-5 | Dihydrocarvyl acetate | |

Cinnamyl derivatives

| CAS Number | Chemical Name | OtherName |
|---|---|---|
| 104-55-2 | Cinnamaldehyde | 2 Propenal, 3-phenyl- |
| 104-54-1 | Cinnamyl alcohol | 2-Propen-1-ol, 3-phenyl- |
| 101-86-0 | alpha-Hexylcinnamaldehyde | Octanal, 2-(phenylmethylene)- |
| 101-39-3 | alpha-Methylcinnamaldehyde | 2-Propenal, 2-methyl-3-phenyl- |
| 103-26-4 | Methyl cinnamate | 2 Propenoic acid, 3-phenyl-, methyl ester |
| 122-97-4 | 3-Phenyl 1-propanol | Benzenepropanol |

Esters of aliphatic acyclic primary alcohols with aliphatic linear saturated carboxylic acids

| CAS Number | Chemical Name | OtherName |
|---|---|---|
| 16491-36-4 | cis-3-Hexenyl butyrate | Butanoic acid, (3Z)-3-hexenyl ester |
| 31501-11-8 | cis-3-Hexenyl hexanoate | Hexanoic acid, (3Z)-3-hexenyl ester |
| 2639-63-6 | Hexyl butyrate | Butanoic acid, hexyl ester |
| 6378-65-0 | Hexyl hexanoate | Hexanoic acid, hexyl ester |
| 2445-76-3 | Hexyl propionate | |
| 110-19-0 | Ixobutyl acetate | |
| 112-19-6 | 10-Undecen-1-yl acetate | |

TABLE 2

| CAS Number | Chemical Name |
|---|---|
| 100-06-1 | Acetanisole |
| 10032-15-2 | Hexyl 2-methylbutanoate |
| 100-86-7 | alpha,alpha-Dimethylphenethyl alcohol |
| 10094-41-4 | 3-Hexenyl 2-methylbutanoate |
| 101-41-7 | Methyl phenylacetate |
| 101-84-8 | Diphenyl ether |
| 101-86-0 | alpha-Hexylcinnamaldehyde |
| 101-94-0 | p-Tolyl phenylacetate |
| 101-97-3 | Ethyl phenylacetate |
| 102-13-6 | Isobutyl phenylacetate |
| 102-16-9 | Benzyl phenylacetate |
| 102-19-2 | Isoamyl phenylacetate |
| 102-22-7 | Geranyl phenylacetate |
| 103-07-1 | 2-Methyl-4-phenyl-2-butyl acetate |
| 103-36-6 | Ethyl cinnamate |
| 103-38-8 | Benzyl isovalerate |
| 103-41-3 | Benzyl cinnamate |
| 103-52-6 | Phenethyl butyrate |
| 103-53-7 | Phenethyl cinnamate |
| 103-54-8 | Cinnamyl acetate |
| 103-56-0 | Cinnamyl propionate |
| 103-59-3 | Cinnamyl isobutyrate |
| 103-60-6 | 2-Phenoxyethyl isobutyrate |
| 103-82-2 | Phenylacetic acid |
| 103-93-5 | p-Tolylisobutyrate |
| 104-09-6 | p-Tolylacetaldehyde |
| 104-20-1 | 4-(p-Methoxyphenyl)-2-butanone |
| 104-21-2 | Anisyl acetate |
| 104-45-0 | p-Propylanisole |
| 104-53-0 | 3-Phenylpropionaldehyde |
| 104-55-2; 14371-10-9 | Cinnamaldehyde |
| 104-57-4 | Benzyl formate |
| 10458-14-7 | Menthone |
| 104-62-1 | Phenethyl formate |
| 104-65-4 | Cinnamyl formate |
| 104-76-7 | 2-Ethyl-1-hexanol |
| 105-01-1 | Isobutyl 3-(2-furan)propionate |
| 105-37-3 | Ethyl propionate |
| 105-57-7 | Acetal |
| 105-68-0 | Isoamyl propionate |
| 105-85-1 | Citronellyl formate |
| 105-86-2 | Geranyl formate |
| 105-90-8 | Geranyl propionate |
| 106-21-8 | 3,7-Dimethyl-1-octanol |

TABLE 2-continued

| CAS Number | Chemical Name |
|---|---|
| 106-22-9 | dl-Citronellol |
| 106-23-0 | Citronellal |
| 106-24-1 | Geraniol |
| 106-29-6 | Geranyl butyrate |
| 106-35-4 | 3-Heptanone |
| 106-44-5 | p-Cresol |
| 106-68-3 | 3-Octanone |
| 106-70-7 | Methyl hexanoate |
| 1076-56-8 | 1-Methyl-3-methoxy-4-isopropylbenzene |
| 107-87-9 | 2-Pentanone |
| 108-21-4 | Isopropyl acetate |
| 108-29-2 | gamma-Valerolactone |
| 108-50-9 | 2,6-Dimethylpyrazine |
| 108-64-5 | Ethyl isovalerate |
| 108-82-7 | 2,6-Dimethyl-4-heptanol |
| 108-83-8 | 2,6-Dimethyl-4-heptanone |
| 109-08-0 | 2-Methylpyrazine |
| 109-19-3 | Butyl isovalerate |
| 109-21-7 | Butyl butyrate |
| 109-42-2 | Butyl 10-undecenoate |
| 109-94-4 | Ethyl formate |
| 110-27-0 | Isopropyl myristate |
| 110-40-7 | Diethyl sebacate |
| 110-43-0 | 2-Heptanone |
| 11050-62-7 | Isojasmone |
| 110-93-0 | 6-Methyl-5-hepten-2-one |
| 111-11-5 | Methyl octanoate |
| 111-13-7 | 2-Octanone |
| 111-62-6 | Ethyl oleate |
| 1117-55-1 | Hexyl octanoate |
| 111-81-9 | Methyl 10-undecenoate |
| 1118-27-0 | Linalyl isovalerate |
| 112-06-1 | Heptyl acetate |
| 112-12-9 | 2-Undecanone |
| 112-14-1 | Octyl acetate |
| 112-17-4 | Decyl acetate |
| 1123-85-9 | beta-Methylphenethyl alcohol |
| 112-38-9 | 10-Undecenoic Acid |
| 112-45-8 | 10-Undecenal |
| 112-66-3 | Lauryl acetate |
| 112-80-1 | Oleic Acid |
| 1128-08-1 | 3-Methyl-2-(n-pentanyl)-2-cyclopenten-1-one |
| 1139-30-6 | beta-Caryophyllene oxide |
| 115-71-9 (α) 77-42-9 (β 11031-45-1) | Santalol |
| 115-95-7 | Linalyl acetate |
| 115-99-1 | Linalyl formate |
| 116-02-9 | 3,5,5-Trimethylcyclohexanol |
| 116-53-0 | 2-Methylbutyric acid |
| 118-58-1 | Benzyl salicylate |
| 118-71-8 | Maltol |
| 119-36-8 | Methyl salicylate |
| 1193-81-3 | (±)-1-Cyclohexylethanol |
| 1195-32-0 | p,alpha-Dimethylstyrene |
| 119-65-3 | Isoquinoline |
| 1197-01-9 | p-alpha, alpha-Trimethylbenzyl alcohol |
| 120-11-6 | Isoeugenyl benzyl ether |
| 120-45-6 | alpha-Methylbenzyl propionate |
| 120-50-3 | Isobutyl benzoate |
| 120-51-4 | Benzyl benzoate |
| 120-57-0 | Piperonal |
| 1207-44-0 | Prenyl benzoate |
| 121-32-4 | Ethyl vanillin |
| 121-33-5 | Vanillin |
| 121-39-1 | Ethyl 3-phenylglycidate |
| 121-98-2 | Methyl anisate |
| 122-40-7 | alpha-Amylcinnamaldehyde |
| 122-48-5 | Zingerone |
| 122-67-8 | Isobutyl cinnamate |
| 122-68-9 | 3-Phenylpropyl cinnamate |
| 122-69-0 | Cinnamyl cinnamate |
| 122-70-3 | Phenethyl propionate |
| 122-72-5 | 3-Phenylpropyl acetate |
| 122-78-1 | Phenylacetaldehyde |
| 122-91-8 | Anisyl formate |
| 123-07-9 | p-Ethylphenol |
| 123-32-0 | 2,5-Dimethylpyrazine |

TABLE 2-continued

| CAS Number | Chemical Name |
|---|---|
| 123-51-3 | Isoamyl alcohol |
| 123-68-2 | Allyl hexanoate |
| 123-76-2 | Levulinic acid |
| 123-86-4 | Butyl acetate |
| 123-92-2 | Isoamyl acetate |
| 124-06-1 | Ethyl myristate |
| 124-10-7 | Methyl myristate |
| 125037-13-0; 502-61-4 | Farnesene |
| 125-12-2 | Isobornyl acetate |
| 126-64-7 | Linalyl benzoate |
| 127-17-3 | Pyruvic acid |
| 127-41-3 | alpha-ionone |
| 127-42-4 | Methyl-alpha-ionone |
| 127-43-5 | Methyl-beta-ionone |
| 127-91-3 | beta-Pinene |
| 13171-00-1 | 4-Acetyl-6-t-butyl-1,1-dimethylindan |
| 1322-17-4 | 1,3-Nonanediol acetate (mixed esters) |
| 133-37-9, 87-69-4 | Tartaric acid (d-, l-, dl-, meso-) |
| 1334-78-7 | Tolualdehydes (mixed o, m, p) |
| 13466-78-9 | 3-Carene |
| 13481-87-3 | Methyl 3-nonenoate |
| 13494-06-9 | 3,4-Dimethyl-1,2-cyclopentadione |
| 13532-18-8 | Methyl 3-methylthiopropionate |
| 13679-70-4 | 5-Methyl-2-thiophenecarboxyaldehyde |
| 13877-91-3 | 3,7-Dimethyl-1,3,6-octatriene |
| 140-11-4 | Benzyl acetate |
| 140-39-6 | p-Tolyl acetate |
| 141-12-8 | Neryl acetate |
| 141-14-0 | Citronellyl propionate |
| 141-16-2 | Citronellyl butyrate |
| 141-92-4 | Hydroxycitronellal dimethyl acetal |
| 142-19-8 | Allyl heptanoate |
| 142-50-7 | Petitgrain Oil |
| 143-13-5 | Nonyl acetate |
| 143-14-6 | 9-Undecenal |
| 143-28-2 | cis-9-Octadecenol |
| 144-39-8 | Linalyl propionate |
| 14765-30-1 | 2-sec-Butylcyclohexanone |
| 148-05-1 | gamma-Dodecalactone |
| 14901-07-6; 79-77-6 | beta-Ionone |
| 150-78-7 | p-Dimethoxybenzene |
| 151-10-0 | m-Dimethoxybenzene |
| 15111-96-3 | p-Mentha-1.8-dien-7-yl acetate |
| 151-82-4 | 3-Hexenyl formate |
| 15356-70-4, 89-78-1, 1490-04-6 | Menthol |
| 15679-13-7 | 2-Isopropyl-4-methylthiazole |
| 15706-73-7 | n-Butyl 2-methylbutyrate |
| 15707-23-0 | 2-Ethyl-3-methylpyrazine |
| 1604-28-0 | 6-Methyl-3,5-heptadien-2-one |
| 1617-23-8 | Ethyl 2-methyl-3-pentenoate |
| 16356-11-9 | 1,3,5-Undecatriene |
| 16409-43-1 | Tetrahydro-4-methyl-2-(2-methylpropen-1-yl)pyran |
| 16491-24-0 | 2,4-Hexadienyl isobutyrate |
| 16510-27-3 | 1-Cyclopropanemethyl-4-methoxybenzene |
| 1786-08-9 | Nerol oxide |
| 1866-31-5 | Allyl cinnamate |
| 197098-61-6 | 8-Ocimenyl acetate |
| 198-24-2 | 1-Octen-3-yl acetate |
| 198404-98-7 | (1-Methyl-2-(1,2,2-trimethylbicyclo[3.1.0]hex-3-ylmethyl)cyclopropyl)methanol |
| 19872-52-7 | 4-Mercapto-4-methyl-2-pentanone |
| 2021-28-5 | Ethyl 3-phenylpropionate |
| 21368-68-3 | dl-Camphor |
| 2142-94-1 | Neryl formate |
| 21722-83-8 | Cyclohexaneethyl acetate |
| 2173-57-1 | beta-Naphthyl isobutyl ether |
| 21834-92-4 | 5-Methyl-2-phenyl-2-hexenal |
| 2236-90-2 | Vanilla (*Vanilla* spp.) |
| 2239-36-8 | Mace oil (Houtt.) |
| 2270-60-2 | Methyl 3,7-dimethyl-6-octenoate |
| 2305-21-7 | 2-Hexen-1-ol |
| 23267-57-4 | beta-Ionone epoxide |
| 2345-26-8 | Geranyl isobutyrate |
| 2408-20-0 | Allyl propionate |
| 24168-70-5 | 2-Methoxy-3-(1-methylpropyl)pyrazine |
| 2416-94-6 | 2,3,6-Trimethylphenol |
| 2463-53-8 | 2-Nonenal |

TABLE 2-continued

| CAS Number | Chemical Name |
|---|---|
| 24683-00-9 | 2-Isobutyl-3-methoxypyrazine |
| 24717-85-9 | Citronellyl 2-methylbut-2-enoate, |
| 24817-51-4 | Phenylethyl 2-methylbutyrate |
| 24851-98-7 | Methyl dihydrojasmonate |
| 2497-18-9 | 2-Hexen-1-yl acetate |
| 25152-85-6 | cis-3-Hexenyl benzoate |
| 25524-95-2 | 5-Hydroxy-7-decenoic acid delta-lactone |
| 2593-35-2 | Benzoin gum, Sumatra |
| 2785-89-9 | 4-Ethylguaiacol |
| 27939-60-2 | (2,4) and (3,5) and (3,6)-Dimethyl-3-cyclohexenylcarbaldehyde |
| 29214-60-6 | Ethyl 2-acetyloctanoate |
| 29350-73-0; 523-47-7 | Cadinene (mixture of isomers) |
| 29548-30-9 | 3,7,11-Trimethyldodeca-2,6,10-trienyl acetate |
| 29895-73-6 | Phenyl acetaldehyde glyceryl acetal |
| 299-35-2 | Methyl N-acetylanthranilate |
| 301-00-8, 112-63-0 | Methyl linoleate & Methyl linolenate (mixture) |
| 30390-50-2 | 4-Decenal |
| 30640-46-1; 1888-90-0 | Mixture of Methyl cyclohexadiene and Methylene cyclohexene |
| 3142-72-1 | 2-Methyl-2-pentenoic acid |
| 3208-40-0 | 2-(3-Phenylpropyl)tetrahydrofuran |
| 326-61-4 | Piperonyl acetate |
| 32764-98-0 | 8-Decen-5-olide |
| 33467-74-2 | cis-3-Hexenyl propionate |
| 3391-86-4 | 1-Octen-3-ol |
| 3452-97-9 | 3,5,5-Trimethyl-1-hexanol |
| 35044-68-9; 23726-92-3; 23726-91-2 | 4-[(2,6,6)-Trimethylcyclohex-1-enyl) but-2-en-4one |
| 3558-60-9 | Methyl phenethyl ether |
| 360676-70-1; 2216-45-7; 17373-93-2 | Methylbenzyl acetate (mixed o, m, p) |
| 36267-71-7 | 5,7-Dihydro-2-methylthieno(3,4-d)pyrimidine |
| 36431-72-8 | Theaspirane |
| 3658-77-3 | 4-Hydroxy-2,5-dimethyl-3(2H)-furanone |
| 3681-71-8 | cis-3-Hexen-1-yl acetate |
| 3738-00-9 | 1,5,5,9-Tetramethyl-13-oxatricyclo(8.3.0.0(4,9))tridecane |
| 37526-88-8 | Benzyl trans-2-methyl-2-butenoate |
| 3777-69-3 | 2-Pentylfuran |
| 38462-22-5 | p-Mentha-8-thiol-3-one |
| 3848-24-6 | 2,3-Hexanedione |
| 39255-32-8 | Ethyl 2-methylpentanoate |
| 39770-05-3 | 9-Decenal |
| 41519-23-7 | cis-3-Hexenyl isobutyrate |
| 4180-23-8 | trans-Anethole |
| 43052-87-5 | alpha-Damascone |
| 431-03-8 | Diacetyl |
| 432-25-7 | 2,6,6-Trimethyl-1&2-cyclohexen-1-carboxaldehyde |
| 4395-92-0 | p-Isopropylphenylacetaldehyde, |
| 459-80-3 | Geranic acid |
| 4602-84-0 | Farnesol |
| 464-49-3 | d-Camphor |
| 4674-50-4 | Nootkatone |
| 4695-62-9 | d-Fenchone |
| 470-67-7 | 1,4-Cineole |
| 470-82-6 | Eucalyptol |
| 472-66-2 | 2,6,6-Trimethyl-1-cyclohexen-1-acetaldehyde |
| 4748-78-1 | 4-Ethylbenzaldehyde |
| 4826-62-4 | 2-Dodecenal |
| 488-10-8, 6261-18-3 | 3-Methyl-2-(2-pentenyl)-2-cyclopenten-1-one |
| 490-03-9 | (+/−) 2-Hydroxypiperitone |
| 491-07-6 | d,l-Isomenthone |
| 4940-11-8 | Ethyl maltol |
| 495-62-5 | Bisabolene |
| 501-52-0 | 3-Phenylpropionic acid |
| 502-47-6 | 3,7-Dimethyl-6-octenoic acid |
| 503-74-2 | Isovaleric acid |
| 507-70-0 | Borneol |
| 513-86-0 | Acetoin |
| 515-03-7 | (−)-Sclareol |
| 527-60-6 | 2,4,6-Trimethylphenol |
| 5320-75-2 | Cinnamyl benzoate |
| 536-59-4 | p-Mentha-1,8-dien-7-ol |
| 536-60-7 | p-Isopropylbenzyl alcohol |
| 5392-40-5 | Citral |
| 539-88-8 | Ethyl levulinate |

TABLE 2-continued

| CAS Number | Chemical Name |
|---|---|
| 539-90-2 | Isobutyl butyrate |
| 540-07-8 | Amyl hexanoate |
| 540-18-1 | Amyl butyrate |
| 5405-41-4 | Ethyl 3-hydroxybutyrate |
| 541-47-9 | 3-Methylcrotonic acid |
| 541-91-3 | 3-Methyl-1-cyclopentadecanone |
| 543-49-7 | 2-Heptanol |
| 544-40-1 | Butyl sulfide |
| 55066-56-3 | p-Tolyl 3-methylbutyrate |
| 55418-52-5 | 4-(3,4-Methylenedioxyphenyl)-2-butanone |
| 556-82-1 | 3-Methyl-2-buten-1-ol |
| 55719-85-2 | Phenethyl tiglate |
| 5579-78-2 | epsilon-Decalactone |
| 56011-02-0 | Isoamyl phenethyl ether |
| 562-74-3 | 4-Carvomenthenol |
| 564-20-5 | Sclareolide |
| 564-94-3 | 2-Formyl-6,6-dimethylbicyclo(3.1.1.)hept-2-ene |
| 5655-61-8 | l-Bornyl acetate |
| 57-10-3 | Palmitic acid |
| 57-11-4 | Stearic acid |
| 57-55-6 | Propylene glycol |
| 576-26-1 | 2,6-Xylenol |
| 5837-78-5 | Ethyl tiglate |
| 589-59-3 | 2-Methylpropyl 3-methylbutyrate |
| 589-66-2 | Isobutyl 2-butenoate |
| 590-86-3 | 3-Methylbutyraldehyde |
| 593-08-8 | 2-Tridecanone |
| 59558-23-5 | p-Tolyl octanoate |
| 5988-91-0 | 3,7-Dimethyloctanal |
| 5989-27-5 | d-Limonene |
| 60047-17-8, 5989-33-3, 34995-77-2 | Linalool oxide |
| 60-12-8 | Phenethyl alcohol |
| 60-33-3 | Linoleic Acid |
| 606-45-1 | Methyl o-methoxybenzoate |
| 621-82-9; 140-10-3 | Cinnamic acid |
| 623-42-7 | Methyl butyrate |
| 624-41-9 | 2-Methylbutyl acetate |
| 628-97-7 | Ethyl palmitate |
| 6290-17-1 | Ethyl 2,4-dimethyl-1,3-dioxolane-2-acetate |
| 6290-37-5 | Phenethyl hexanoate |
| 63449-68-3 | beta-Naphthyl anthranilate |
| 638-49-3 | Amyl formate |
| 6413-10-1 | Ethyl acetoacetate ethyleneglycol ketal |
| 64275-73-6 | cis-5-Octen-1-ol |
| 644-35-9 | o-Propylphenol |
| 645-13-6 | p-Isopropylacetophenone |
| 645-56-7 | p-Propylphenol |
| 65416-14-0 | Maltyl isobutyrate |
| 65620-50-0 | 6-Hydroxydihydrotheaspirane |
| 65-85-0 | Benzoic acid |
| 659-70-1 | Isoamyl isovalerate |
| 67028-40-4 | Ethyl (p-tolyloxy)acetate |
| 67-63-0 | Isopropyl alcohol |
| 67634-23-5 | 2-Phenylpropanal propyleneglycol acetal |
| 67674-36-6 | 2,6-Nonadienal diethyl acetal |
| 67715-80-4 | 2-Methyl-4-propyl-1,3-oxathiane |
| 67801-20-1 | 3-Methyl-5-(2,2,3-trimethylcyclopent-3-en-1-yl)pent-4-en-2-ol |
| 67801-45-0 | trans-3-Heptenyl 2-methylpropanoate |
| 67883-79-8 | cis-3-Hexenyl tiglate |
| 6789-88-4 | Hexyl benzoate |
| 68398-18-5 | (+/−) 2,8-Epithio-cis-p-menthane |
| 68606-81-5 | Currant buds black absolute (*Ribes nigrum* L.) |
| 68606-83-7 | Cananga oil |
| 68648-39-5 | Oils, lemon, terpene-free |
| 68917-18-0 | Cornmint Oil |
| 68917-52-2 | Schinus molle oil (*Schinus molle* L.) |
| 68917-75-9 | Wintergreen oil (*Gaultheria procumbens* L.) |
| 68952-43-2 | Oils, star anise |
| 689-67-8 | 6,10-Dimethyl-5,9-undecadien-2-one |
| 692-86-4 | Ethyl 10-undecenoate |
| 698-10-2 | 5-Ethyl-3-hydroxy-4-methyl-2(5H)-furanone |
| 698-76-0 | delta-Octalactone |
| 7011-83-8 | gamma-Methyldecalactone |
| 705-73-7 | alpha-Propylphenethyl alcohol |
| 70851-61-5 | 4-Hydroxy-4-methyl-7-cis-decenoic acid gamma lactone |

TABLE 2-continued

| CAS Number | Chemical Name |
|---|---|
| 71159-90-5 | 1-p-Menthene-8-thiol |
| 713-95-1 | delta-Dodecalactone |
| 71-41-0 | Amyl alcohol |
| 7452-79-1 | Ethyl 2-methylbutyrate |
| 7492-44-6 | alpha-Butylcinnamaldehyde |
| 7492-67-3 | Citronelloxyacetaldehyde |
| 7492-70-8 | Butyl butyryllactate |
| 7493-57-4 | Propyl phenethyl acetal |
| 7493-74-5 | Allyl phenoxyacetate |
| 75-18-3 | Methyl sulfide |
| 7549-33-9 | Anisyl propionate |
| 7549-37-3 | Citral dimethyl acetal |
| 76-49-3 | Bornyl acetate |
| 77-53-2 | (+)-Cedrol |
| 7779-23-9 | Linalyl hexanoate |
| 7779-50-2, 28645-51-4, 123-69-3 | omega-6-Hexadecenlactone |
| 7779-65-9 | Isoamyl cinnamate |
| 7779-78-4 | alpha-Isobutylphenethyl alcohol |
| 7779-81-9 | Isobutyl angelate |
| 77-83-8 | Ethyl methylphenylglycidate |
| 7785-33-3 | Geranyl tiglate |
| 7786-29-0 | 2-Methyloctanal |
| 7786-44-9 | 2,6-Nonadien-1-ol |
| 7786-61-0 | 2-Methoxy-4-vinylphenol |
| 78-35-3 | Linalyl isobutyrate |
| 78-37-5 | Linalyl cinnamate |
| 78-70-6 | Linalool |
| 78-84-2 | Isobutyraldehyde |
| 79-09-4 | Propionic acid |
| 79-31-2 | Isobutyric acid |
| 79-69-6 | alpha-Irone |
| 79-76-5 | gamma-Ionone |
| 79-89-0 | beta-Isomethylionone |
| 79-92-5 | Camphene |
| 8000-25-7 | Oils, rosemary |
| 8000-26-8 | Pine needle oil |
| 8000-28-0 | Oils, lavender |
| 8000-29-1 | Oil of Citronella, *Cymbopogon nardus* (1.) Rendle (Sri Lanka type) |
| 8000-29-1 | Oil of citronella, *Cymbopogon winterianus* Jowitt (Java type) |
| 8000-46-2 | Oils, geranium |
| 8000-48-4 | Eucalyptus oil |
| 8000-66-6 | Cardamom seed oil (*Elettaria cardamomum* (L.) Maton) |
| 8002-68-4 | Juniper oil (*Juniperus communis* L.) |
| 8002-73-1 | Orris absolute (*Iris pallida*) |
| 8006-64-2 | Turpentine, oil |
| 8006-77-7 | Allspice oil (*Pimento officinalis* Lindl.) |
| 8006-82-4 | Pepper, black, oil (*Piper nigrum* L.) |
| 8006-83-5 | Hyssop oil (Hyssopus officinalis L.) |
| 8006-84-6 | Fennel oil bitter (*Foeniculum vulgare* Miller) |
| 8006-90-4 | Oils, peppermint |
| 8007-00-9 | Balsam oil, Peru (*Myroxylon pereirae* Klotzach) |
| 8007-01-0 | Rose absolute (*Rosa* spp.) |
| 8007-11-2 | Origanum oil, Spanish |
| 8007-35-0 | Terpinyl acetate |
| 8007-46-3 | Oils, thyme |
| 8007-70-3 | Oil of anise |
| 8007-75-8 | Oil of bergamot |
| 8007-80-5 | Cassia bark oil |
| 8008-51-3 | Oil of camphor |
| 8008-52-4 | Coriander oil (*Coriandrum sativum* L.) |
| 8008-57-9 | Oil of orange |
| 8008-80-8 | Oils, spruce |
| 8008-98-8 | Cajeput oil (*Melaleuca leucadendron* L.) |
| 8014-19-5 | Oils, palmarosa |
| 8014-29-7 | Rue oil (*Ruta graveolens* L.) |
| 8015-77-8 | Bois de rose oil |
| 8015-92-7 | Chamomile flower, Romary oil (*Anthemis nobilis* L.) |
| 8016-21-5 | Cognac oil, green |
| 8016-31-7 | Lovage oil (*Levisticum officinale* Koch) |

TABLE 2-continued

| CAS Number | Chemical Name |
|---|---|
| 8016-38-4 | Neroli bigarde oil (*Citrus aurantium* L.) |
| 8016-44-2 | Petitgrain Paraguay oil |
| 8016-63-5 | Clary oil (*Salvia sclarea* L.) |
| 8016-78-2 | Sandalwood yellow oil (*Santalum album* L.) |
| 8016-78-2 | Spike lavender oil (*Lavandula* spp.) |
| 8016-84-0 | Tagetes oil (*Tagetes erecta* L.) |
| 8021-29-2 | Oils, Fir |
| 8022-56-8 | Oils, sage (Spanish) |
| 8022-96-6 | Jasmine oil (*Jasminum grandiflorum* L.) |
| 8023-95-8 | Helichrysum leaf oil (*Helichrysum angustifolium*) |
| 8023-99-2 | Pine scotch oil (*Pinus sylvestris* L.) |
| 8024-05-3 | Tuberose oil (*Polianthes tuberosa* L.) |
| 80-27-3 | Terpinyl propionate |
| 8030-28-2 | Orange flower water absolute |
| 8046-19-3 | Storax (*Liquidambar* spp.) |
| 80-56-8 | alpha-Pinene |
| 80-59-1 | trans-2-Methyl-2-butenoic acid |
| 80-71-7 | Methylcyclopentenolone |
| 821-55-6 | 2-Nonanone |
| 83-34-1 | Skatole |
| 84082-70-2 | Peppermint (*Mentha piperita*) ext. |
| 84649-98-9 | Cinnamon leaf oil |
| 84650-63-5 | Vanilla extract (*Vanilla*spp.) |
| 84929-51-1 | Thyme (*Thymus vulgaris*) oil |
| 84961-50-2 | Cloves (*Eugenia* spp.) |
| 85940-32-5 | Cardamom (*Elettaria cardamomum* (L.) Maton) |
| 868-57-5 | Methyl 2-methylbutyrate |
| 87-19-4 | Isobutyl salicylate |
| 87-20-7 | Isoamyl salicylate |
| 87-22-9 | Phenethyl salicylate |
| 87-25-2 | Ethyl anthranilate |
| 87-44-5 | beta-Caryophyllene |
| 87-91-2 | Diethyl tartrate |
| 88-69-7 | 2-Isopropylphenol |
| 88-84-6 | Guaiene |
| 89-79-2 | Isopulegol |
| 89-83-8 | Thymol |
| 9000-64-0 | Tolu, balsam, gum (*Myroxylon* spp.) |
| 90-02-8 | Salicylaldehyde |
| 90-05-1 | Guaiacol |
| 90-12-0 | 1-Methylnaphthalene |
| 90147-36-7 | Violet leaves absolute (*Viola odorata* L.) |
| 91-10-1 | 2,6-Dimethoxyphenol |
| 91-16-7 | 1,2-Dimethoxy benzene |
| 91-62-3 | 6-Methylquinoline |
| 92-52-4 | Biphenyl |
| 928-96-1 | 3-Hexen-1-ol |
| 93-04-9 | beta-Naphthyl methyl ether |
| 93-08-3 | Methyl beta-naphthyl ketone |
| 93-16-3 | Isoeugenyl methyl ether |
| 93-18-5 | beta-Naphthyl ethyl ether |
| 93-28-7 | Eugenyl acetate |
| 93-29-8 | Isoeugenyl acetate |
| 93-51-6 | 2-Methoxy-4-methylphenol |
| 94-02-0 | Ethyl benzoylacetate |
| 94087-83-9 | 4-Methoxy-2-methyl-2-butanethiol |
| 94167-14-3 | Vanilla tahitensis, ext. |
| 94266-47-4 | Citrus, ext. |
| 94-46-2 | Isoamyl benzoate |
| 94-48-4 | Geranyl benzoate |
| 94-86-0 | Propenylguaethol |
| 95-16-9 | Benzothiazole |
| 95-65-8 | 3,4-Xylenol |
| 95-87-4 | 2,5-Xylenol |
| 96-48-0 | 4-Hydroxybutanoic acid lactone |
| 97-42-7 | Carvyl acetate |
| 97-53-0 | Eugenol |
| 97-54-1 | Isoeugenol |
| 97-64-3 | Ethyl lactate |
| 97-89-2 | Citronellyl isobutyrate |
| 98-01-1 | Furfural |
| 98-02-2 | Furfuryl mercaptan |
| 99-72-9 | 2-(p-Tolyl)propionaldehyde |
| 997-29-7 | Valencene |

TABLE 2-continued

| CAS Number | Chemical Name |
|---|---|
| 99-83-2 | alpha-Phellandrene |
| 99-86-5 | p-Mentha-1,3-diene |

Water

The compositions disclosed herein may comprise water. The water may be of any hardness. The water may be de-ionized water, reverse-osmosis-treated water, distilled water, or soft water (typically, soft water does not exceed 40 ppm hardness (as $CaCO_3$)). The amount of water in a given composition depends on the degree to which the composition is concentrated. A concentrate composition may comprise less than about 50% water, usually from about 40% to 75%, or from about 50% to 60% of water by weight of the composition. The concentrate may provide improved economics on a per-use basis (e.g., following recommended dilution) for the user. It is found that even at water content levels of about 50%, the compositions of the invention show surprisingly good hydrolytic stability (octyl sulfate reversion to octanol+sulfuric acid).

Ready-to-use compositions generally comprise greater water content than concentrated compositions, which are intended to be diluted at the point of use. A ready-to-use composition may comprise from about 80% to about 99.9%, or from about 90% to about 99.5% water, or from about 91% to about 99% water by weight of the composition.

pH

The compositions disclosed herein have pH values ranging from about 1.5 to about 5.0, or from about 2 to about 4, or from about 2.1 to about 3.5. For a concentrated composition that comprises less than 70% water, the pH is measured after adding de-ionized water to the composition, until the total water concentration in the composition is 70%. For compositions that comprise greater than or equal to 70% water, pH is measured on the composition as made (the composition is not diluted prior to measuring the pH).

An exemplary concentrate composition comprises:
   a) from about 3% to about 15% by weight of the composition of octanoic acid and from about 5% to about 10% by weight of the composition of a secondary acid having a pKa below 4, preferably the secondary acid is selected from the group consisting of citric acid, lactic acid and mixtures thereof;
   b) from about 12% to about 20% by weight of the composition of octyl sulfate and from about 2% to about 6% by weight of the composition of sodium lauryl sulfate; and
   c) from about 5% to about 20% by weight of the composition of 2-phenoxyethanol or from about 0.1 to about 5% by weight of the composition of a fragrance.

Another exemplary concentrate composition comprises:
   a) from about 5% to about 10% by weight of the composition of octanoic acid and from about 6% to about 12% by weight of the composition of a secondary acid having a pKa below 4, preferably the secondary acid is selected from the group consisting of citric acid, lactic acid and mixture thereof, more preferably the secondary acid comprises lactic acid;
   b) from about 12% to about 20% by weight of the composition of octyl sulfate and from about 2% to about 6% by weight of the composition of a secondary surfactant having a hydrophobic moiety comprising a carbon chain length with at least twelve carbon atoms; and
   c) from about 0.1% to about 5% by weight of the composition of a fragrance.

Another exemplary concentrate composition comprises:
   a) from about 4% to about 12% by weight of the composition of octanoic acid from about 5% to about 12% by weight of the composition of an acid selected from the group consisting of lactic acid, citric acid and mixtures thereof;
   b) from about 10% to about 15% by weight of the composition of octyl sulfate and from about 2% to about 6% by weight of the composition of lauryl sulfate; and
   c) from about 0.1% to about 5% by weight of the composition of a fragrance.

Another exemplary ready-to-use composition comprises:
   a) from about 0.05% to about 1% by weight of the composition of octanoic acid and from about 0.5% to about 5% by weight of the composition of a secondary acid having a pKa below 4, preferably the secondary acid is selected from the group consisting of citric acid, lactic acid and mixtures thereof;
   b) from about 1% to about 5% by weight of the composition of octyl sulfate and from about 0.1% to about 2% by weight of the composition of a secondary surfactant having a hydrophobic moiety comprising a carbon chain length with at least twelve carbon atoms; and
   c) from about 0.1% to about 5% by weight of the composition of 2-phenoxyethanol.

Another exemplary ready-to-use composition comprises:
   a) from about 0.05% to about 0.6% by weight of the composition of octanoic acid and from about 0.5% to about 3% by weight of the composition of a secondary acid selected from the group consisting of lactic acid, citric acid and mixtures thereof;
   b) from about 1% to about 4% by weight of the composition of octyl sulfate and from about 0.1% to about 1% by weight of the composition of a secondary surfactant having a hydrophobic moiety comprising a carbon chain length with at least twelve carbon atoms; and
   c) from about 0.01% to about 0.5% by weight of the composition of fragrance.

Adjuncts

The compositions disclosed herein may also contain one or more adjuncts. Adjuncts may be employed to increase immediate and/or residual efficacy of the compositions, improve the wetting characteristics of the compositions upon application to a target substrate, operate as solvents for diluted compositions, and/or serve to modify the aesthetic characteristics of the composition. These adjuncts may also provide degreasing and solubilizing benefits, additional antimicrobial potentiation, suds control, thickening, soil agglomeration or soil release benefits, enhanced composition solubility, freeze-thaw stability, further catalysis of antimicrobial activity, residual or long-lasting (e.g., 24 hours) duration antimicrobial properties and/or enhanced surface safety benefits.

The composition(s) disclosed herein may comprise an adjunct selected from the group consisting of chelants, builders, buffers, abrasives, electrolytes, bleaching agents, dyes, foaming control agents, corrosion inhibitors, essential oils, thickeners, pigments, gloss enhancers, enzymes, detergents, solvents, dispersants, polymers, silicones, hydrotropes (e.g., sodium toluene, sodium xylene or sodium cumene sulfonate), and mixtures thereof.

In one embodiment, the composition of the invention is approved to clean and disinfect food-contact surfaces. As such, selection of approved food-contact surface adjuncts is needed to ensure that the complete composition consists only of approved food use active and inert ingredients. This includes fragrances and fragrances, which are usually composed of a large blend of individual raw materials. In another embodiment, each of the fragrance raw materials is approved for use on food contact surfaces. Use on contact use surfaces allows for product application on hard surfaces without the need for a rinse step.

Methods of Use

The compositions disclosed herein may be used in a variety of applications and methods, including the treatment of inanimate surfaces, e.g. hard surfaces. The compositions may be used in the home to clean, sanitize, disinfect and/or sterilize hard surfaces, such as counters, sinks, restrooms, toilets, bathtubs, shower stalls, kitchen appliances, restaurant tables and seats, countertops, floors, windows, walls, furniture, phones, toys, drains, pipes, and the like. The compositions may also be used in commercial establishments, such as hotels, hospitals, care homes, eating establishments, fitness centers, schools, office buildings, department stores, and prisons, to clean, sanitize, disinfect, or sterilize equipment, tools, food and medical preparation areas (in addition to the surfaces mentioned above that are common to both homes and commercial establishments). The compositions disclosed herein may be used to treat indoor as well as outdoor inanimate surfaces and may also be used to sanitize, disinfect, and/or sterilize soft inanimate surfaces, such as carpets, area rugs, curtains, upholstery, and clothes, in both home and commercial settings.

The compositions may be used to kill or inactivate bacteria, non-enveloped or enveloped viruses, fungi, mycobacteria, spores, or allergens on surfaces or in the air. The compositions may also be used to purify contaminated water. The compositions may be used to disinfect or sanitize indoor or outdoor non-food, indirect food, or food contact agricultural premises, buildings, including animal housing, pens, feed troughs, greenhouses, storage containers and the like. The compositions may be used to sanitize and/or disinfect equipment used in non-food, indirect food, or food contact indoor and outdoor settings, including equipment used in green houses (with or without ornamental or food crops), feed handling, hatcheries, ice dispensing, processing livestock feeding, milk processing, milking, mushroom houses, poultry processing or handling, transport vehicles, and the like. The compositions may also be used to clean and disinfect food and non-food contact surfaces in consumer homes and in commercial establishments, including but not limited to, kitchens, front and back of restaurants, cafeterias, cafes, bars, hotel lobbies and rooms, commercial establishment bathrooms, conference rooms, workplace desks and benches, care home areas, and the like.

Ready-to-use compositions may be housed in any container that allows for dispensing. Such containers may be metered to dispense a desired quantity or may include devices, such as caps, that allow the user to determine the level of dosing. Examples of containers include bottles, aerosols, pumps, and the like. Ready-to-use compositions may also be embedded in wipes or foams, such as melamine-formaldehyde foams. Such wipes may comprise woven and/or nonwoven substrates, where the substrates may include synthetic fibers, non-synthetic fibers, or mixtures of synthetic and non-synthetic fibers. As such, the wipe may optionally comprise cellulosic or non-cellulosic fibers, and, for high chemical resistance, may be in the form of a microfiber. The wipe may be a stand-alone or singly-formed substrate or a laminate of two or more substrates. The concentrate may be housed in any container as well. In one example, the concentrate is housed in a PET bottle, preferably made from recycled PET. The concentrate may be dosed using mechanical or electrical pumps.

The composition(s) disclosed herein can be in a spray dispenser or in a nonwoven substrate. The spray bottle may be a 2-chamber bottle in which, for example, the antimicrobial active is present in a first chamber and is separated from other formulation components present in the second chamber so as to mitigate or preclude reactivity of the antimicrobial active prior to use. For example, the 2-chamber bottle can be used to reduce or eliminate equilibrium ester formation from reaction octanoic acid with 2-phenoxyethanol or with specific fragrance components. Upon spraying, the contents of the 2 chambers are mixed together and sprayed as a uniform solution. The present disclosure also relates to a method of reducing the population of microorganism on a surface comprising the steps of applying an effective amount of the composition(s) disclosed herein to the surface and optionally wiping the surface. The present disclosure also relates to a method of reducing population of microorganism on a surface comprising the steps of applying an effective amount of the composition(s) disclosed herein to the surface, where the composition contacts the surface for about 30 seconds to about 2 minutes, and optionally wiping the surface.

The methods of the invention provide fast disinfection as measured using the US EPA protocol for the Germicidal Spray Test versus Gram (+) bacteria such as *Staphylococcus aureus* and Gram (−) bacteria such as *Pseudomonas aeruginosa* using a one-minute exposure time. The methods provide fast fungicidal activity using the US EPA protocol for the Germicidal Spray Test versus *Trichophyton interdigitale* at a two-minute exposure time. The methods also provide fast virucidal activity using the US EPA protocol for the Germicidal Spray Test vs. non-enveloped viruses such as Rhinovirus and Feline calicivirus (Norovirus surrogate) and Murine Norovirus at 15 second and 30 second exposure times.

EXAMPLES

For purposes of illustrating the benefits provided by the compositions of the invention, bactericidal, fungicidal and virucidal tests were performed. The bactericidal and fungicidal activity of the compositions of the present disclosure was quantified by the Association of Official Analytical Chemists (AOAC) Germicidal Spray Test (GST) Official Method 961.02, Germicidal Spray Products as Disinfectants (Official Methods of Analysis of the AOAC, 2009 Edition). Briefly, the GST is a carrier-based method used to evaluate disinfection efficacy of aerosol/pump-based spray products and volatile liquid products. In this method, a series of glass slides ("carriers") are inoculated with a representative test organism and dried for 30 minutes (>4 log inoculation). The carriers contacting the dried organism film are then sequentially treated with the spray product until thoroughly wet and are exposed for a finite contact time. After exposure, the carriers are sequentially transferred to a liquid subculture medium specifically selected to neutralize the test substance antimicrobial active and to recover any surviving test organism. The carriers are incubated and visually examined for the presence or absence of growth. Results are recorded as: number of carriers showing growth/number of carriers tested. For example, a test result with 2 carriers showing growth out of 60 carriers tested would be recorded as 2/60; it is understood that a lower number of carriers showing growth is suggestive of a stronger performance, with 0/60 being the best result achievable. As such, comparisons may be made to differentiate the cidal efficacy of different compositions at a given contact time. In examples below, the exposure (contact) time for each experiment or group of experiments is provided. The virucidal activity of the compositions of the invention is measured using the EPA Virucidal Hard Surface Efficacy Test. Briefly, 8 glass Petri dishes with marked 4 square inches are inoculated with 0.4 ml of the challenge microorganism and dried for 30 minutes. Inoculated carriers are then sprayed until thoroughly wet, from a distance of 6 to 8 inches, with each pre-diluted composition using AOAC hard water (400 ppm as $CaCO_3$) or de-ionized water. The carriers include 5% serum organic load and the exposure time is either 15 or 30 seconds.

The compositions below were made up by mixing the components together. The concentration of each component in a given composition corresponds to the weight of the component, provided on an active basis, as a percent of the mass of the composition. Thus, '7% citric acid' means that the composition contains 7 grams citric acid active per 100 grams total mass of the composition. The components were added in the following order: de-ionized water, then sodium octyl sulfate and other surfactants, then organic acid(s), then octanoic acid, then optional fragrance or 2-phenoxyethanol and other optional adjuncts. The compositions were heated to about 50° C. to accelerate dissolution of components though this is not a requisite step. All compositions were stored at ambient conditions (20-23° C.) prior to testing.

For the Germicidal Spray Test results, the following microorganism abbreviations are used:
SA=*Staphylococcus aureus* ATCC 6538
PA=*Pseudomonas aeruginosa* ATCC 15442
TI=*Trichophyton interdigitale* ATCC 9533

For the Virucidal Hard Surface Efficacy Test, the following microorganism abbreviations are used:
RV 14=Rhinovirus Type 14 ATCC VR-284
FCV=Feline calicivirus—ATCC VR-782
MNS=Murine Norovirus, Strain 99 (from Friedlich-Loeffer-Institut)

Just prior to testing, the concentrate compositions were diluted in either 400 ppm hardness AOAC synthetic water expressed as $CaCO_3$ ('Hard Water') or de-ionized water (abbreviated 'DI $H_2O$'). The methodology is described in the Association of Official Analytical Chemists (AOAC), Official Method 960.09, Germicidal and Detergent Sanitizing Action of Disinfectants, Preparation of Synthetic Hard Water, in Official Methods of Analysis of the AOAC, 2005 Edition. Dilutions are made on a volume basis. A 1:40 dilution means that a ready-to-test solution is made by combining with 39 milliliters of water for each milliliter of the composition to be diluted. Carrier results for bactericidal and fungicidal tests are reported as the number of carriers showing growth divided by the total number of carriers. Carrier results for virucidal tests are reported as a $log_{10}$ reduction number.

Abbreviations

C8 AS: Sodium octyl sulfate, tradename Stepanol® C-8 sulfate from the Stepan Company, supplied as a 33% active solution in water.

C12-14 AS: Sodium lauryl sulfate, tradename Stepanol® WA-Extra from the Stepan Company, supplied as a 29% solution in water.

Citric acid: Citric acid, from Tate & Lyle Corporation, supplied as a 50% solution in water Lactic acid: Lactic acid, from Sigma-Millipore supplied as an 88% solution in water.

Octanoic acid: Octanoic acid, tradename C8-99K, from Procter & Gamble, supplied as a 99+% neat liquid.

2-EPh: 2-Phenoxyethanol, tradename Phenoxitol®, from Univar supplied as a 99+% neat liquid.

PMA: Polymaleic acid, tradename Dequest P9000, from Italmatch supplied as a 50% amber solution in water.

PAA: Polyacrylic acid, tradename Acumer 1020, from Dow Chemical, supplied as a 40% solution in water.

Benzoic acid: ACS reagent benzoic acid supplied as a soft pellets by Sigma-Millipore with a minimum 99.5% activity.

NaCS: Sodium cumene sulfonate, tradename Naxonate® SC from Nease Corporation, supplied as a 45% solution in water.

Compositions #1-9 Testing:

Germicidal spray tests are performed in hard water conditions. Testing results are at 1-minute exposure time, unless stated otherwise, (SA=*Staphylococcus aureus* ATCC 6538, PA=*Pseudomonas aeruginosa* ATCC 15442, TI=*Trichophyton interdigitale* ATCC 9533). Microorganism inoculum count was ≥6 log for SA and PA testing, and ≥5 log for TI testing Concentrate Compositions #1-3:

| Ingredient | # 1 (wt %) | # 2 (wt %) | # 3 (wt %) |
|---|---|---|---|
| C8 AS | 15.0 | 15.0 | 15.0 |
| C12-14 AS | 3.5 | 3.5 | 3.5 |
| Citric Acid | 8.4 | — | — |
| Lactic Acid | — | 8.4 | 8.4 |
| Octanoic Acid | 7.0 | 7.0 | 7.0 |
| NaCS | 7.0 | 7.0 | 7.0 |
| 2-EPh | — | — | 16.0 |
| Fragrance | 1.5 | 1.5 | — |
| DI H2O | Remainder | Remainder | Remainder |
| pH | 2.3 | 2.5 | 2.9 |

| Composition # | SA 1:40 dilution Hard water | PA 1:40 dilution Hard water | TI 1:40 dilution Hard water |
|---|---|---|---|
| 1 | 0/60 | 0/60 | 0/30 |
| 2 | 0/60 | 0/60 | 0/30 |
| 3 | 0/60 | 0/60 | 0/30 |

Upon dilution, compositions 1-3 of the invention provide complete kill results (e.g., no observed carrier failures). Additionally, compositions 1-3 all use US EPA inert food contact raw materials.

Ready-To-Use Compositions #4-6

Germicidal spray tests results are at 30 seconds exposure time for composition 4 and 5, and at 15 seconds exposure time for composition 6.

| Ingredient | # 4 (wt %) | # 5 (wt %) | # 6 (wt %) |
|---|---|---|---|
| C8 AS | 3.0 | 3.0 | 2.0 |
| C12-14 AS | 0.4 | 0.4 | 0.7 |
| Lactic Acid | 1.0 | 1.0 | — |
| Citric Acid | — | — | 1.0 |
| Octanoic Acid | 0.3 | 0.6 | 0.6 |
| 2-EPh | — | 4.0 | 4.0 |
| DI H2O | Remainder | Remainder | Remainder |
| pH | 2.3 | 2.3 | 2.3 |

| Composition # | SA | PA | TI |
|---|---|---|---|
| 4 | 0/60 | 0/60 | 0/30 |
| 5 | 0/60 | 0/60 | 0/30 |
| 6 | 0/60 | Not Tested | 0/10 |

Composition #4 and #5 of the invention provide complete kill activity vs. bacteria and fungi at 30 seconds exposure time. Composition #6 shows complete kill activity vs. bacteria and fungi at 15 seconds contact time.

Compositions #1, #3 and #5 Virucidal Testing

The effectiveness of compositions 3 (concentrate, diluted 1:40 in AOAC hard water) and 5 (ready-to-use, undiluted) is evaluated versus three non-enveloped viruses as follows:

Rhinovirus Type 14 (RV 14)—ATCC VR-284 and Feline calicivirus (FCV)—ATCC VR-782. & Murine Norovirus, Strain 99 (MNS). Composition performance is measured using the EPA Virucidal Hard-Surface Efficacy Test. Briefly, 8 glass petri dishes with marked areas of 4 square inches are inoculated with 0.4 ml of the challenge microorganism and dried for 30 minutes. Inoculated carriers are then sprayed until thoroughly wet, from a distance of 6 to 8 inches. Composition 3 is pre-diluted 1:40 in AOAC hard water (400 ppm $CaCO_3$). The carriers include a 5% serum organic load and the exposure time is 15 seconds at 20±2° C.

Composition 1
1:40 dilution, Hard $H_2O$

| | Carrier Result | Log Reduction | Conclusion |
|---|---|---|---|
| MNS | Not requested | 3.50 | Passed |
| FCV | 0/8 failures | ≥7.75 | Passed |

Composition 3
1:40 dilution, Hard $H_2O$

| | Carrier Result | Log Reduction | Conclusion |
|---|---|---|---|
| RV 14 | 0/8 failures | ≥4.00 | Passed |
| FCV | 0/8 failures | ≥7.75 | Passed |

Composition 5
No dilution

| | Carrier Result | Log Reduction | Conclusion |
|---|---|---|---|
| RV 14 | 0/8 failures | ≥4.00 | Passed |
| FCV | 0/8 failures | ≥7.75 | Passed |

Composition #1 diluted 1:40 in AOAC hard water passes the Virucidal Hard-Surface Efficacy Test versus Feline calicivirus and Murine Norovirus at a 15 second contact time. Composition #3 diluted 1:40 in AOAC hard water and composition #5, undiluted, pass the Virucidal Hard-Surface Efficacy Test versus Rhinovirus Type 14, and versus Feline calicivirus at a 15 second contact time with complete virus inactivation.

Concentrate Compositions #7-9:

| Ingredient | # 7 (wt %) | # 8 (wt %) | # 9 (wt %) |
|---|---|---|---|
| C8 AS | 12.0 | 12.0 | 12.0 |
| C12-14 AS | 2.0 | 2.0 | 2.0 |
| Polymaleic acid | 7.0 | 7.0 | — |
| Benzoic acid | — | 3.0 | — |
| Polyacrylic acid | — | — | 7.0 |
| Octanoic Acid | 7.0 | 7.0 | 5.0 |
| Fragrance | 1.0 | 1.0 | 0.5 |
| DI H2O | Remainder | Remainder | Remainder |
| pH | 2.1 | 2.1 | 2.1 |

| Composition # | SA 1:40 dilution Hard Water | PA 1:40 dilution Hard Water | TI 1:40 dilution Hard Water |
|---|---|---|---|
| 7 | 0/60 | 0/60 | 0/30 |
| 8 | 1/60 | 0/60 | 0/30 |
| 9 | 0/60 | 0/60 | 0/30 |

Compositions 7-9 diluted 1:40 in AOAC hard water demonstrate the ability to use a polymeric acid and still deliver bactericidal and moldicidal benefits.

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

What is claimed is:
1. An antimicrobial composition comprising:
   a) an acid system comprising at least 30% by weight thereof of octanoic acid and a secondary acid;

b) from about 10% to 30% by weight of the composition of an anionic surfactant system comprising from about 75% to 90% by weight thereof of octyl sulfate and at least 10% by weight thereof of a secondary surfactant having a moiety comprising a carbon chain length with at least 12 carbon atoms is dodecyl sulfate, lauryl sulfate or both; and c) a fragrance;

and wherein:
the composition has a pH of from about 1.5 to about 5 as measured at 20° C., and
the composition is stable in concentrate having from about 40% to about 75% water and upon dilution having from about 80% to about 99.9% water.

2. A composition according to claim 1 comprising:
from about 10% to about 30% by weight of the composition of the acid system;
and
from about 0.1% to about 5% by weight of the composition of the fragrance;
and wherein the composition has a pH of from about 2 to about 4 as measured at 20° C.

3. A composition according to claim 1 comprising:
from about 10% to about 30% by weight of the composition of the acid system;
at least 10% by weight thereof of dodecyl sulfate; and
from about 0.1% to about 5% by weight of the composition of the fragrance;
and wherein the composition has a pH of from about 2 to about 4 as measured at 20° C.

4. A composition according to claim 1 wherein the composition comprises from about 12% to about 22% by weight of the composition of the acid system and wherein the acid system comprises from about 35% to about 55% by weight thereof of octanoic acid and the secondary acid has a pKa of 4 or below at 20° C.

5. A composition according to claim 1 wherein the composition comprises from about 12% to about 22% by weight of the composition of the surfactant system and wherein the surfactant system comprises from about 75% to about 90% by weight thereof of octyl sulfate and from about 10% to 30% by weight of secondary surfactant, dodecyl sulfate, lauryl sulfate or both.

6. A composition according to claim 1 comprising from about 0.1% to about 3% by weight of the composition of the fragrance.

7. A composition according to claim 1 comprising:
from about 4% to about 12% by weight of the composition of octanoic acid and from about 5% to about 12% by weight of the composition of a secondary acid having a pKa below 4 at 20° C.;
from about 10% to about 20% by weight of the composition of octyl sulfate and from about 2% to about 6% by weight of the composition of a secondary surfactant having a moiety comprising a carbon chain length with at least twelve carbon atoms is dodecyl sulfate, lauryl sulfate or both; and
from about 0.1% to about 3% by weight of the composition of the fragrance.

8. A composition according to claim 1 comprising:
from about 0.5% to about 4% by weight of the composition of the acid system comprising at least 30% by weight thereof of octanoic acid;
and
from 0.1% to about 3% by weight of the composition of the fragrance.

9. A composition according to claim 1 wherein the composition comprises from about 1% to about 4% by weight of the composition of the acid system and wherein the acid system comprises from about 35% to about 45% by weight thereof of octanoic acid and the secondary acid has a pKa of 4 or below at 20° C.

10. The composition according to claim 1 wherein the composition comprises:
from about 0.1% to about 2% by weight of the composition of octanoic acid and from about 0.5% to about 5% by weight of the composition of a secondary acid having a pKa below 4 as measured at 20° C.;
and
from about 0.1% to about 3% by weight of the composition of the fragrance.

11. An antimicrobial composition comprising:
a) an acid system comprising at least 30% by weight thereof of octanoic acid and a secondary acid;
b) from about 10% to 30% by weight of the composition of an anionic surfactant system comprising from about 75% to 90% by weight thereof of octyl sulfate and at least 10% by weight thereof of a secondary surfactant having a moiety comprising a carbon chain length with at least 12 carbon atoms is dodecyl sulfate, lauryl sulfate or both; and
c) 2-phenoxyethanol;
and wherein:
the composition has a pH of from about 1.5 to about 5 as measured at 20° C., and the composition is stable in concentrate having from about 40% to about 75% water and upon dilution having from about 80% to about 99.9% water.

12. A composition according to claim 11 comprising:
from about 10% to about 30% by weight of the composition of the acid system wherein the acid system comprises from about 35% to about 55% by weight thereof of octanoic acid and the secondary acid has a pKa of 4 or below at 20° C.;
and
from about 10% to about 30% by weight of the composition of 2-phenoxyethanol;
and wherein the composition has a pH of from about 2 to about 4 as measured at 20° C.

13. A composition according to claim 11 comprising:
from about 4% to about 12% by weight of the composition of octanoic acid and from about 5% to about 12% by weight of the composition of a secondary acid having a pKa below 4 at 20° C.;
from about 10% to about 20% by weight of the composition of octyl sulfate and from about 2% to about 6% by weight of the composition of a secondary surfactant having a moiety comprising a carbon chain length with at least twelve carbon atoms; and
from about 10% to about 20% by weight of the composition of 2-phenoxyethanol.

14. A composition according to claim 11 comprising:
from about 0.5% to about 4% by weight of the composition of the acid system comprising at least 30% by weight thereof of octanoic acid;
and
from about 10% to about 20% by weight of the composition of 2-phenoxyethanol.

15. A composition according to claim 11 wherein the composition comprises from about 1% to about 4% by weight of the composition of the acid system and wherein the acid system comprises from about 35% to about 45% by weight thereof of octanoic acid and the secondary acid has a pKa of 4 or below at 20° C.

16. The composition according to claim 12 wherein the composition comprises:
   from about 0.1% to about 2% by weight of the composition of octanoic acid;
   and
   from about 1% to about 6% by weight of the composition of 2-phenoxyethanol.

17. A method of treating an inanimate surface comprising the steps of:
   i) diluting in water a composition according to claim 1 to make an aqueous solution; and
   ii) contacting the surface with the solution.

18. A method of treating an inanimate surface with the antimicrobial composition according to claim 1 to provide biocidal activity vs. Gram (+) bacteria such as *Staphylococcus aureus* and Gram (−) bacteria such as *Pseudomonas aeruginosa* wherein the biocidal activity is measured using a one minute exposure time following the US EPA protocol for the Germicidal Spray Test.

* * * * *